(12) United States Patent
Kyvik et al.

(10) Patent No.: US 9,248,259 B2
(45) Date of Patent: Feb. 2, 2016

(54) DOUBLE NOTCHED CATHETER SECUREMENT ASSEMBLY

(71) Applicant: TIDI Securement Products, LLC, Neenah, WI (US)

(72) Inventors: Kurt Kyvik, Satellite Beach, FL (US); Arthur Parkhurst, Ocala, FL (US)

(73) Assignee: TIDI Securement Products, LLC, Neenah, WI (US)

( * ) Notice: Subject to any disclaimer, the term of this patent is extended or adjusted under 35 U.S.C. 154(b) by 157 days.

(21) Appl. No.: 13/966,970

(22) Filed: Aug. 14, 2013

(65) Prior Publication Data

US 2015/0051549 A1     Feb. 19, 2015

(51) Int. Cl.
*A61M 25/02*     (2006.01)

(52) U.S. Cl.
CPC ....... *A61M 25/02* (2013.01); *A61M 2025/0246* (2013.01); *A61M 2025/0253* (2013.01); *A61M 2025/0266* (2013.01); *A61M 2025/0273* (2013.01)

(58) Field of Classification Search
CPC ............ A61M 25/02; A61M 2025/0253; A61M 2025/0266; A61M 2025/0273; A61M 5/14248; A61M 2025/0246
See application file for complete search history.

(56) References Cited

U.S. PATENT DOCUMENTS

| | | |
|---|---|---|
| 3,138,158 A | 6/1964 | Gordon et al. |
| 3,167,072 A | 1/1965 | Stone et al. |
| 3,826,254 A | 7/1974 | Mellor |
| 3,834,380 A | 9/1974 | Boyd |
| 3,918,446 A | 11/1975 | Buttaravoli |
| 3,973,565 A | 8/1976 | Steer |
| 4,129,128 A | 12/1978 | McFarlane |
| 4,250,880 A | 2/1981 | Gordon |
| 4,460,356 A | 7/1984 | Moseley |
| 4,490,141 A | 12/1984 | Lacko et al. |
| 4,519,793 A | 5/1985 | Galindo |
| 4,699,616 A | 10/1987 | Nowak et al. |
| 4,717,385 A | 1/1988 | Cameron et al. |
| 4,767,411 A | 8/1988 | Edmunds |
| 4,822,342 A | 4/1989 | Brawner |
| 4,838,868 A | 6/1989 | Forgar et al. |
| 4,863,432 A | 9/1989 | Kvalo |
| 4,874,380 A | 10/1989 | Hesketh |
| 4,915,694 A | 4/1990 | Yamamoto et al. |
| 5,037,397 A | 8/1991 | Kalk et al. |
| 5,192,274 A | 3/1993 | Bierman |
| 5,215,532 A | 6/1993 | Atkinson |
| 5,219,336 A | 6/1993 | Wilk |
| 5,224,935 A | 7/1993 | Hollands |

(Continued)

FOREIGN PATENT DOCUMENTS

| | | |
|---|---|---|
| CN | 203123273 | 8/2013 |
| DE | 20020326 U1 | 2/2001 |

(Continued)

*Primary Examiner* — Nicholas Lucchesi
*Assistant Examiner* — Justin L Zamory
(74) *Attorney, Agent, or Firm* — Boyle Fredrickson, S.C.

(57) ABSTRACT

A catheter securement device that adheres to the skin of a patient having an epidural catheter or similar small flexible tube member inserted percutaneously, the securement device having a flexible, sheet-like main body member capable of adhering to the skin of the patient, a double notched pad member over which the catheter is bent, and a releasable retention member to secure the catheter onto the main body member.

19 Claims, 5 Drawing Sheets

(56) References Cited

U.S. PATENT DOCUMENTS

| | | |
|---|---|---|
| 5,232,453 A | 8/1993 | Plass et al. |
| 5,236,421 A | 8/1993 | Becher |
| 5,282,791 A | 2/1994 | Lipton et al. |
| 5,370,627 A | 12/1994 | Conway |
| 5,380,294 A | 1/1995 | Persson |
| 5,413,562 A | 5/1995 | Swauger |
| 5,685,859 A | 11/1997 | Kornerup |
| 6,273,873 B1 | 8/2001 | Fleisher |
| 6,419,660 B1 | 7/2002 | Russo |
| 6,428,516 B1 | 8/2002 | Bierman |
| D470,936 S | 2/2003 | Bierman |
| 6,689,104 B2 | 2/2004 | Bierman |
| D492,411 S | 6/2004 | Bierman |
| 6,765,122 B1 | 7/2004 | Stout |
| 6,770,055 B2 | 8/2004 | Bierman et al. |
| 6,827,706 B2 | 12/2004 | Tollini |
| 6,837,875 B1 | 1/2005 | Bierman |
| 6,866,652 B2 | 3/2005 | Bierman |
| D503,977 S | 4/2005 | Bierman |
| 6,875,200 B1 | 4/2005 | Ajagbe |
| 6,929,625 B2 | 8/2005 | Bierman |
| 6,951,550 B2 | 10/2005 | Bierman |
| 6,979,320 B2 | 12/2005 | Bierman |
| 7,018,362 B2 | 3/2006 | Bierman et al. |
| D528,206 S | 9/2006 | Bierman |
| 7,137,968 B1 | 11/2006 | Burrell et al. |
| 7,524,307 B2 | 4/2009 | Davis et al. |
| 7,637,894 B2 | 12/2009 | Fleisher |
| D608,444 S | 1/2010 | Kyvik et al. |
| D608,887 S | 1/2010 | Kyvik et al. |
| 7,648,485 B2 | 1/2010 | Fleisher |
| D616,091 S | 5/2010 | Kyvik et al. |
| D616,542 S | 5/2010 | Kyvik et al. |
| D616,983 S | 6/2010 | Kyvik et al. |
| 7,766,880 B1 | 8/2010 | Spinoza |
| D625,002 S | 10/2010 | Kyvik et al. |
| 7,812,212 B2 | 10/2010 | Propp et al. |
| D652,509 S | 1/2012 | Kyvik et al. |
| 8,128,602 B2 | 3/2012 | Tollini et al. |
| 8,157,770 B2 | 4/2012 | Elwell et al. |
| D663,834 S | 7/2012 | Kyvik et al. |
| 8,241,253 B2 | 8/2012 | Bracken |
| 8,251,957 B2 | 8/2012 | Kyvik et al. |
| 8,500,698 B2 | 8/2013 | Kyvik et al. |
| 8,608,706 B2 | 12/2013 | Davis et al. |
| 8,834,427 B2 | 9/2014 | Kyvik et al. |
| D715,927 S | 10/2014 | Kyvik et al. |
| D715,928 S | 10/2014 | Kyvik et al. |
| 2002/0195114 A1 | 12/2002 | Tollini |
| 2008/0132821 A1* | 6/2008 | Propp .................. A61M 25/02 602/54 |
| 2009/0137961 A1* | 5/2009 | Bracken ................ A61M 25/02 604/177 |
| 2010/0298778 A1 | 11/2010 | Bracken |
| 2011/0021997 A1 | 1/2011 | Kyvik et al. |
| 2012/0083743 A1* | 4/2012 | Kyvik .................. A61M 25/02 604/180 |
| 2012/0316504 A1 | 12/2012 | Kyvik et al. |
| 2013/0096507 A1 | 4/2013 | Lelievre |
| 2013/0150796 A1 | 6/2013 | Souza et al. |

FOREIGN PATENT DOCUMENTS

| | | |
|---|---|---|
| EP | 0408389 | 1/1991 |
| GB | 2464662 A | 4/2010 |

* cited by examiner

DOUBLE NOTCHED CATHETER SECUREMENT ASSEMBLY

BACKGROUND OF THE INVENTION

This invention relates generally to the field of medical devices referred to as catheter securement devices, a catheter being defined herein to include a small diameter, flexible tube that is inserted through a person's skin and into a vein to deliver or remove fluids such as blood, saline solutions, medications, etc. A catheter securement device typically comprises a flexible sheet member adhesively adhered to the patient's skin, the device having means to retain the catheter tubing or a catheter housing, often a coupling or junction member for connecting one tube to another or to multiple tubes, in a relatively stable manner such that it is less likely for the catheter to be accidentally pulled from the patient.

Catheter securement devices are often located a short distance from the insertion site, such that the securement device has a minimal or reduced effect in securing the catheter tube in place at the actual insertion site. It is an object of this invention to provide a catheter securement device that reduces the likelihood of accidental dislodgement of the catheter by providing a structure that allows the securement device to be located close to or at the insertion site, the device being provided with a pair of opposing notches in a pad member for better securement of the catheter.

SUMMARY OF THE INVENTION

The invention is a catheter securement device adapted to be adhesively adhered to the skin of a patient, the device comprising a flexible sheet-like main body member, a lower adhesive layer disposed on the underside of the main body member, an upper adhesive layer disposed on the upper side of the main body member, a flexible sheet, flap or strap catheter retention member mounted to the upper side of the main body member by a portion of the upper adhesive layer, the flexible retention member having a fixed end and a releasable end, and a double notched catheter pad member also mounted on the upper side of and extending across the main body member, preferably utilizing the upper adhesive layer, the notches being on opposite sides of the pad member. The retention member and pad member are arranged such that the retention member overlays the pad member, and the retention member is provided with at least one and preferably a pair of opposing notches, one notch preferably larger than the other, that correspond in position to the notches in the pad member. The pad upper surface is provided with an adhesive layer. Preferably the main body member is also provided with a pair of notches corresponding to the notches in the pad member.

The catheter securement device is adhered to the patient such that a first notch is positioned adjacent or near the catheter insertion site. The catheter is brought up through the first notch, positioned transversely across the main body member, and then positioned down through the second notch. The flexible retention member is then brought over the catheter and secured, the retention member pressing the catheter into an exposed portion of the pad member upper surface adhesive layer. The retention member is provided with a notch of greater size than the pad member first notch to reduce pressure being applied to the catheter where it extends from the skin. The flexible retention member may be releasably fastened utilizing the upper adhesive layer, or the flexible retention member may be held in closed position by a hook assembly member, the hook assembly member and the retention member combining to form a hook-and-loop-type fastener. The retention member may also be formed of a transparent or translucent material to enable visual inspection of the retained catheter. The pad member is preferably composed of a foam material.

A clear conception of the advantages and features constituting the present invention, and of the construction and operation of typical mechanism provided with the present invention, will become more readily apparent by referring to the exemplary, and therefore non-limiting, embodiments illustrated in the drawings accompanying and forming apart of this specification. wherein like numerals designate the same elements in the several views, and which:

DETAILED DESCRIPTION OF THE INVENTION

Figure 1:
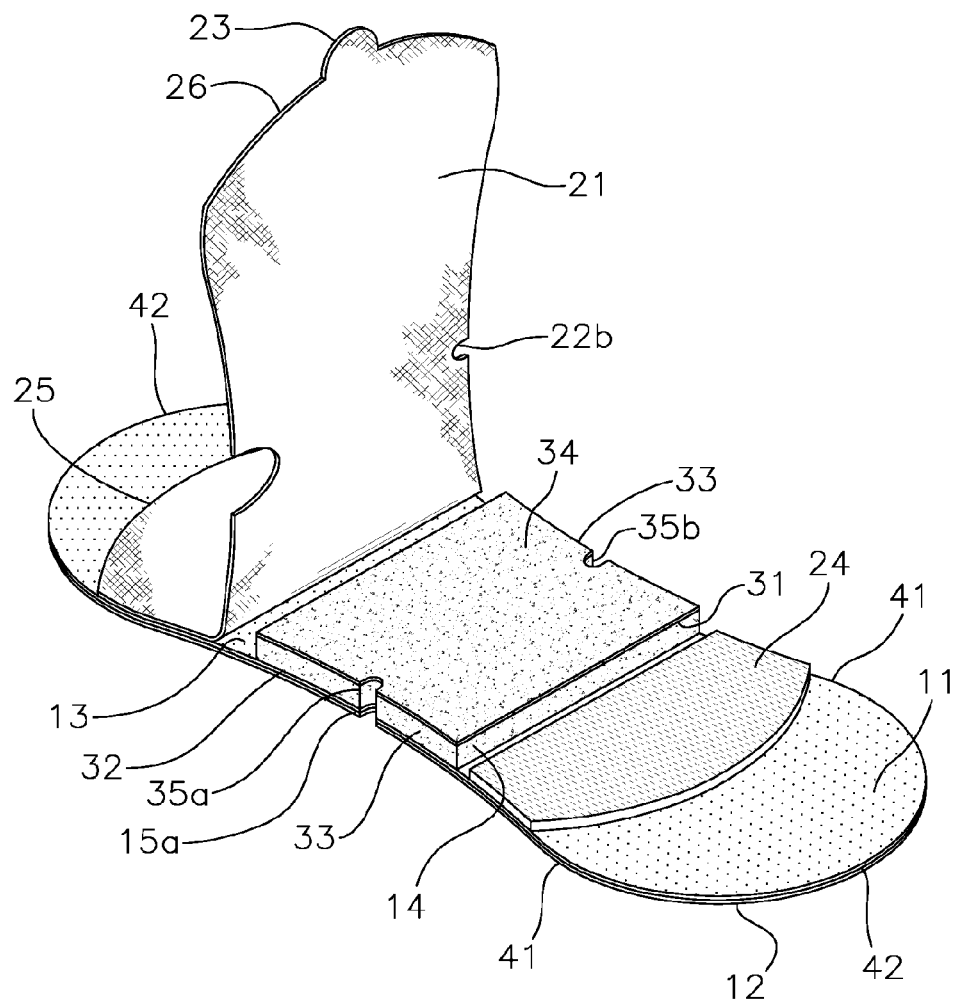
FIG. 1 is a perspective view of an embodiment of the device, shown in the open position prior to closure of the catheter retention member.
Figure 4:
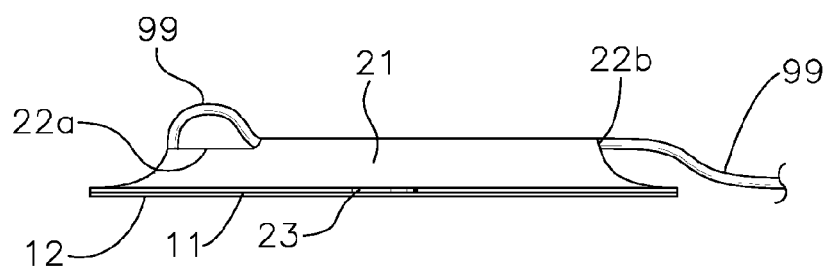
FIG. 4 is an end view of the device of FIG. 2.
Figure 2:
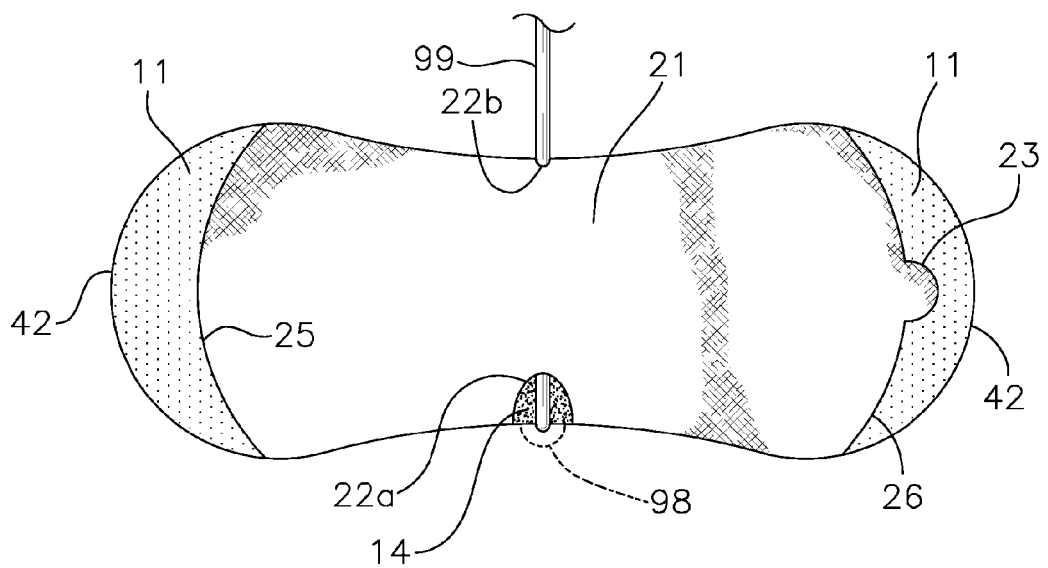
FIG. 2 is a top view of the device of FIG. 1, shown in the use position after closure of the catheter retention member to secure the catheter.
Figure 3:
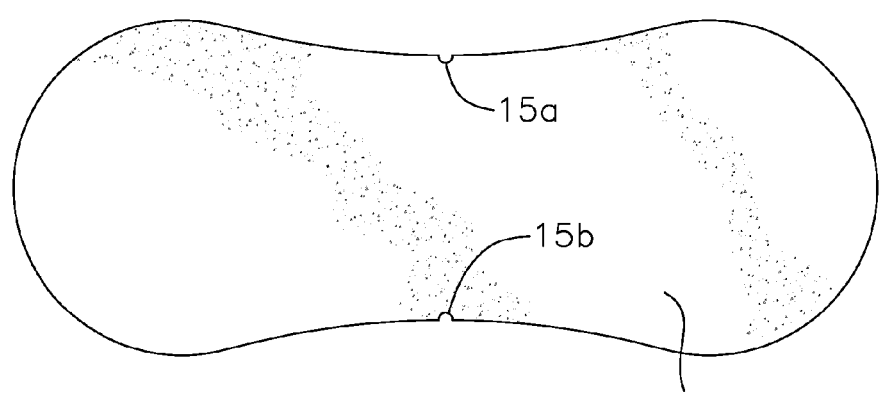
FIG. 3 is a bottom view of the device of FIG. 1.

With reference to the drawings, the invention will now be described in detail with regard for the best mode and the preferred embodiment. In general, the invention is a catheter securement device that adheres to the skin of a patient having an epidural catheter or similar small flexible tube member inserted percutaneously, the securement device acting to secure and retain the catheter to prevent or reduce movement near the insertion site or accidental dislodgement of the catheter. The securement device in general comprises a flexible, sheet-like main body member capable of adhering to the skin of the patient, a double notched pad member over which the catheter is bent, and releasable retention member to secure the catheter onto the main body member.

The catheter securement device comprises a main body member 11. The main body member 11 is a flexible, thin, sheet-like member, generally elongated preferably into a dog-bone-style configuration with two sides 41, preferably concave, and two ends 42, preferably rounded, the main body member 11 being shorter in transverse or lateral direction than in the longitudinal direction. The main body member 11 is preferably formed of a synthetic fabric material.

A lower adhesive layer 12, preferably composed of a hypoallergenic pressure sensitive adhesive (PSA), is disposed on the underside of main body member 11, and most preferably covers the entire underside of main body member 11. The lower adhesive layer 12 is chosen from the class of adhesives which are suitable to removably adhere the main body member 11 to the skin of the patient.

An upper adhesive layer 13, also preferably composed of a hypoallergenic pressure sensitive adhesive (PSA), is disposed on the upper side of main body member 11, and preferably does not cover the entire upper surface of the main body member 11 such that portions of the main body member 11 adjacent the ends 42 are not covered with adhesive. Most preferably, the upper adhesive layer 13 extends completely across the central portion of the main body member 11 in the transverse or lateral direction, i.e., from one side 41 to the other side 41.

A catheter pad member 14 is adhered to the upper surface of the main body member 11 completely across the central portion of the main body member 11 utilizing a portion of the upper adhesive layer 13. The pad member 14 is preferably composed of a compressible synthetic foam material. The pad member 14 comprises an upper surface 31, a lower surface 32 and a pair of opposing exposed edges 33. The pad member 14 is mounted onto the main body member 11 such that the pad exposed edges 33 are positioned at the sides 41 of the main body member 11 The pad member 14 is wider and longer than the main body member edge recess and upper adhesive edge recess, such that a portion of the upper adhesive layer 13 will adhere to the pad lower surface 32 along the three interior edges of the pad member 14. The pad upper surface 31 is preferably provided with an adhesive layer 34. The transverse width of the pad member 14 is substantially equal to the transverse width of the main body member 11.

The pad member 14 further comprises a pair of opposing notches 35a and 35b disposed in the exposed edges 33 and extending completely through the depth of the pad member 14 from the upper surface 31 of the pad member 14 to the lower surface 32 of the pad member 14. The notches 35a and 35b extend a short distance transversely toward the interior of the pad member 14. Preferably the notches 35a and 35b have a generally V-shaped or U-shaped open interior, although other shapes such as circular, oblong, rounded, etc. are suitable alternatives. The notches 35a and 35b are preferably the same size and configuration, but may differ. A first notch 35a is adapted to receive or cradle the catheter 99 extending upwardly from the insertion site 98 and bent transversely across the pad member 14, while the second notch 35b is adapted to provide for a downward slope to the portion of the catheter 99 extending from the opposite exposed edge 33 of the pad member 14.

Most preferably the main body member 11 is also provided with a pair of opposing notches 15a and 15b corresponding in location to the pad member notches 35. The main body notches 15a and 15b are preferably generally the same size and configuration as the pad member notches 35a and 35b, but may also be of different size and shape.

Connected to the main body member 11 by a portion of the upper adhesive, layer 13 is a thin, flexible catheter retention member 21 in the form of a sheet, flap or strap. The retention member 21 has a fixed end 25 and a releasable end 26, the retention member 21 being positioned such that in a closed position it overlaps catheter pad member 14. The retention member 21 preferably is shorter in the longitudinal direction that the main body member 11 and preferably is generally equal in width to the main body member 11 at corresponding points so as to match the peripheral configuration. One side of the retention member 21 is provided with a retention member notch or recess 22a corresponding in location to the pad member first notch 35a, the retention member notch 22a preferably being of greater size than the pad member first notch 35a. Most preferably, the other side of the retention member 21 is provided with a second notch or recess 22b, corresponding in location to the second pad member notch 35b The catheter retention member 21 may also be provided with a tab member 23 on its releasable end 26 for easier closing and opening. The retention member 21 is preferably composed of a synthetic fabric material, and in alternative embodiments the retention member 21 may have a transparent window or be made of transparent material in order to provide visual access to the retained catheter 99 without need for releasing the retention member 21.

In the embodiment as depicted, the catheter securement device is further provided with a hook assembly member 24 mounted onto the main body member 11 by a portion of the upper adhesive layer 13. The hook assembly member 24 is positioned on the opposite side of the pad member 14 from the fixed end 25 of the retention member 21. The hook assembly member 24 and the underside of the releasable end 26 of the retention member 21 together cooperate to form a hook-and-loop-type fastener. In an alternative embodiment, no hook assembly member 24 is present, and the underside of the releasable end 26 of the retention member 21 makes direct contact with a portion of the upper adhesive layer 13.

Figure 5:
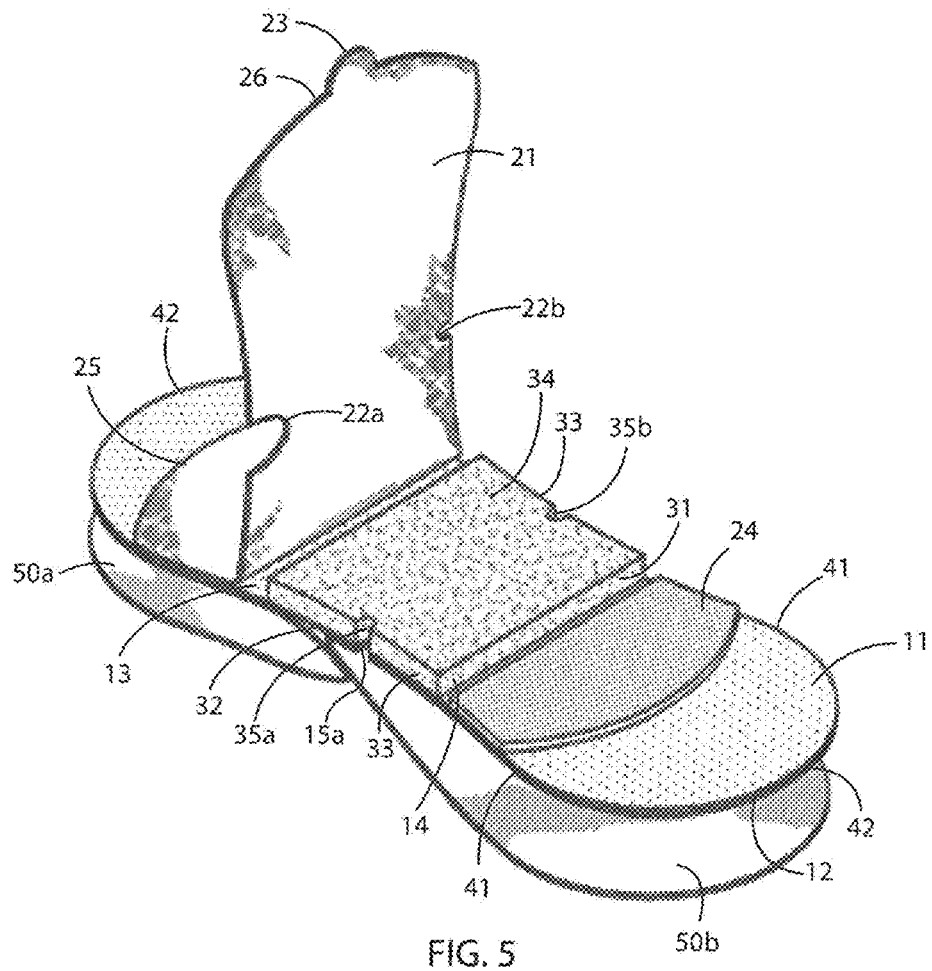
FIG. 5 is a top perspective view of the catheter securement device with release layer shown in the open position.
Figure 6:
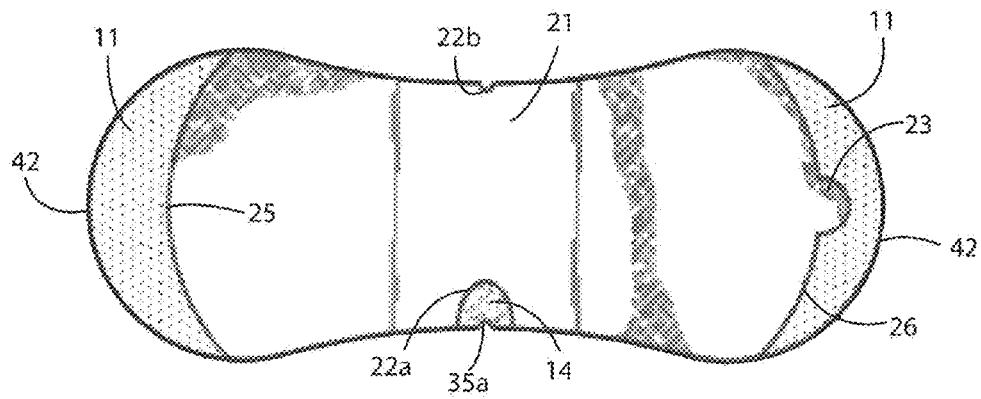
FIG. 6 is a top view of the catheter securement device with release layer of FIG. 5.
Figure 7:
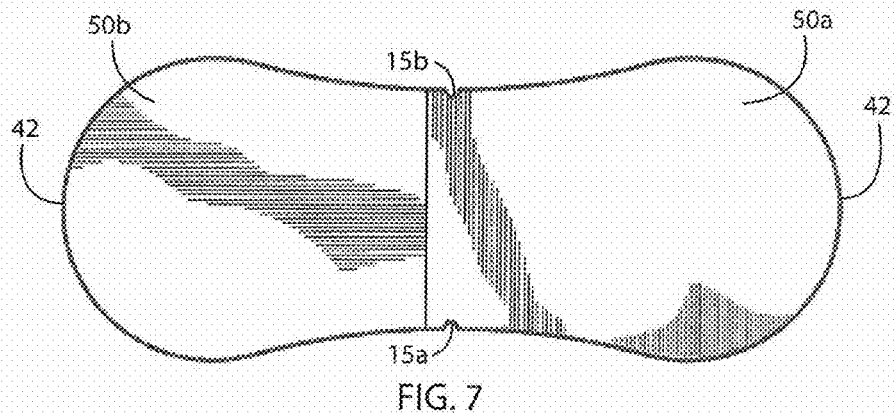
FIG. 7 is a bottom view of the catheter securement device with release layer of FIG. 5.
Figure 8:
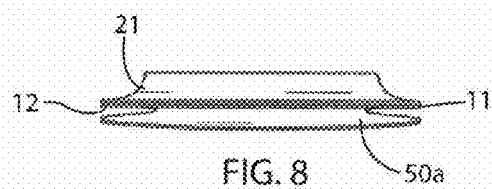
FIG. 8 is a right side view of the catheter securement device with release layer of FIG. 5.
Figure 9:
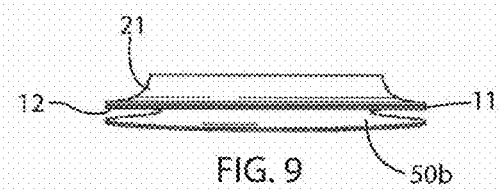
FIG. 9 is a left side view of the catheter securement device, with release layer of FIG. 5.
Figure 10:
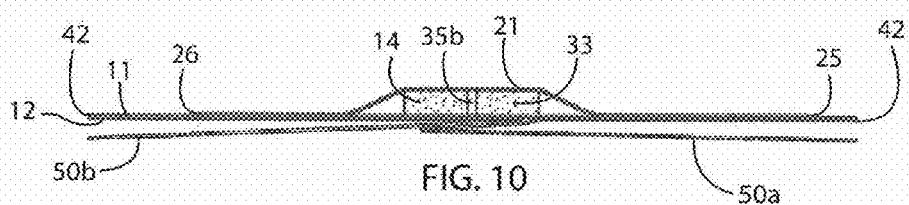
FIG. 10 is a rear view of the catheter securement device with release layer of FIG. 5.
Figure 11:
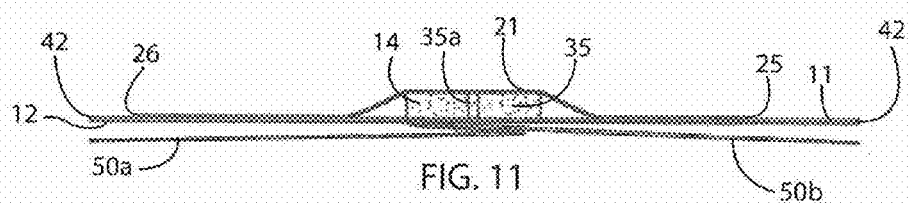
FIG. 11 is a front view of the catheter securement device with release, layer of FIG. 5.
Figure 12:
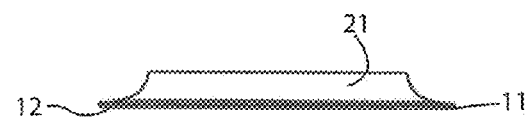
FIG. 12 is a right side view of the catheter securement device with the release layer removed.
Figure 13:
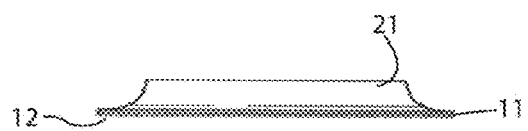
FIG. 13 is a left side view of the catheter securement device with the release layer removed.
Figure 14:
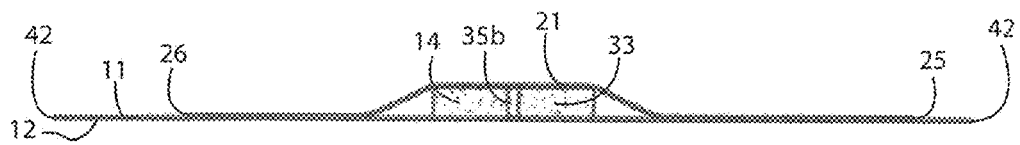
FIG. 14 is a rear view of the catheter securement device with the release layer removed.
Figure 15:
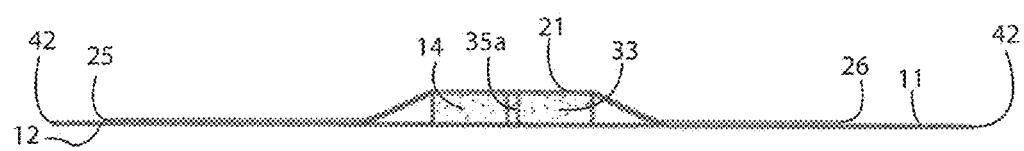
FIG. 15 a front view of the catheter securement device with the release layer removed.

For use the catheter securement device is packaged with release layers 50a, 50b, for instance as shown in one embodiment in FIGS. 5-11, positioned on the exposed adhesive surfaces, the release layers being removed for use, for instance as shown in FIGS. 12-15, as is well known in the art. The catheter securement device is adhered to the patient's skin such that the main body member 11 is located at or adjacent the catheter insertion site 98, such that the first notch 35a receives or cradles a portion of the catheter 99 extending upwardly from the insertion site 98. The catheter 99 is then bent sideways to extend transversely across the main body member 11 above the pad member 14 and pressed into the upper adhesive layer 34. The, catheter 99 is aligned with the second notch 35b. The retention member 21 is then brought down snuggly across the catheter 99 and its releasable end 26 is temporarily secured to the main body member 11 utilizing the hook assembly member 24. The retention member 21 maintains the catheter in contact with the pad upper surface 31, thereby securing the catheter 99 in a controlled manner and maintaining alignment of the catheter 99 with the second notch 35b such that a downward slope can be readily imparted to the catheter 99 to bring it back onto the patient's skin for additional securing using adhesive strips or the like. The presence of a retention member notch 22a of greater dimension than the pad member first notch 35a increases comfort to the patient by not tightly compressing the catheter 99 at the bending region, thereby allowing a larger loop to be present in the catheter 99 prior to its compression by the retention member 21.

It is to be understood that equivalents and substitutions to elements and structures set forth above, which are not intended to be limiting unless necessary for patentability, may be obvious to those of ordinary skill in the art, and therefore the true scope and definition of the invention is to be as set forth in the following claims.

We claim:
1. A catheter securement device comprising:
   a thin, flexible main body member comprising two sides, two ends, an upper side, an underside;
   a lower adhesive layer disposed on the underside of said main body member;
   an upper adhesive layer disposed on the upper side of said main body member;
   a pad member mounted onto said main body member, said pad member extending transversely across said main body member from one of the two sides to the other of the two sides and comprising a pair of opposing exposed edges, a first notch disposed in one of said exposed edges and a second notch disposed in the other of said exposed edges, a pad upper surface and a pad lower surface, said pad upper surface having an adhesive layer thereon;
   wherein said pad member first and second notches extend completely through said pad member from said pad upper surface to said pad lower surface; and
   a retention member comprising a fixed end mounted onto said main, body member and a releasable end, said releasable end being releasably joined to said main body member on the opposite side of said pad member from said fixed end whereby said retention member extends across said pad member.
2. The device of claim 1, further comprising a hook assembly member mounted on said upper side of said main body member by a portion of said upper layer adhesive, said releasable end of said retention member being releasably joined to said main body member by said hook assembly member.
3. The device of claim 1, said retention member further comprising a retention member notch corresponding in location to said pad member first notch.
4. The device of claim 3, wherein said retention member notch is larger than said pad member first notch.
5. The device of claim 1, wherein said lower adhesive layer covers the entire said underside of said main body member, and wherein said upper adhesive layer covers only a portion of said upper side of said main body member, such that the portion of said upper side of said main body member adjacent said main body ends are not covered by adhesive.
6. The device of claim 1, said retention member further comprising a retention member first notch corresponding in location to said pad member first notch and a retention member second notch corresponding in location to said pad member second notch.
7. The device, of claim 6, wherein said retention member first notch is larger than said pad member first notch.
8. The device of claim 1, said main body member further comprising a main body first notch corresponding in location to said pad member first notch and a main body second notch corresponding in location to said pad member second notch.
9. The device of claim 1, wherein said releasable end of said retention member is releasably joined to said main body member by a portion of said upper adhesive layer.
10. A catheter securement device comprising:
    a thin, flexible main body member comprising two sides, two ends, an upper side, an underside and a first notch disposed on one of said sides and a second notch disposed on the other of said sides;
    a lower adhesive layer disposed on the underside of said main body member;
    an upper adhesive layer disposed on a portion of the upper side of said main body member;
    a pad member affixed to said main body member by a portion of said upper adhesive layer, said pad member comprising a pad upper surface, a pad lower surface, a pair of pad exposed edges, a first pad member notch disposed in one of said pad exposed edges and corresponding in location to said main body first notch, and a second pad member notch disposed in the other of said pad exposed edges corresponding in location to said second main body notch;
    a retention member comprising a fixed end mounted onto said main body member and a releasable end, said releasable end being releasably joined to said main body member on the opposite side of said pad member from said fixed end.
11. The device of claim 10, further comprising a hook assembly member mounted on said upper side of said main body member by a portion of said upper layer adhesive, said releasable end of said retention member being releasably joined to said main body member by said hook assembly member.
12. The device of claim 10, said retention member further comprising a retention member notch corresponding m location to said pad member first notch.
13. The device of claim 12, wherein said retention member notch is larger than said pad member first notch.
14. The device of claim 10, said retention member further comprising a retention member first notch corresponding in location to said pad member first notch and a retention member second notch corresponding in location to said pad member second notch.
15. The device of claim 14, wherein said retention member first notch is larger than said pad member first notch.
16. The device of claim 9, wherein said releasable end of said retention member is releasably joined to said main body member by a portion of said upper adhesive layer.
17. A catheter securement device comprising:
    a thin, flexible main body member comprising two sides, two ends, an upper side, an underside and a first notch disposed on one of said sides and a second notch disposed on the other of said sides;
    a lower adhesive layer disposed on the underside of said main body member;
    an upper adhesive layer disposed on a portion of the upper side of said main body member;
    a pad member affixed to said main body member by a portion of said upper adhesive layer, said pad member comprising a pad upper surface, a pad lower surface, a pair of pad exposed edges, a first pad member notch disposed in one of said pad exposed edges and corresponding in location to said main body first notch, and a second pad member notch disposed in the other of said pad exposed edges corresponding in location to said second main body notch;
    a retention member comprising a fixed end mounted onto said main body member and a releasable end, said releasable end being releasably joined to said main body member on the opposite side of said pad member from said fixed end, said retention member further comprising a retention member first notch corresponding in location to said pad member first notch and a retention member second notch corresponding in location, to said pad member second notch, wherein said retention member first notch is larger than said pad member first notch;
    a hook assembly member mounted on said upper side of said main body member by a portion of said upper layer adhesive, said releasable end of said retention member being releasably joined to said main body member by said hook assembly member.
18. The device of claim 17, wherein said lower adhesive layer covers the entire said underside of said main body member, and wherein said upper adhesive layer covers only a portion of said upper side of said main body member, such that the portion of said upper side of said main body member adjacent said main body ends are not covered by adhesive.
19. The device of claim 1, further comprising a hook assembly member mounted on said upper side of said main body member by a portion of said upper layer adhesive, said releasable end of said retention member being releasably joined to said main body member by said hook assembly member and by a portion of said upper adhesive layer;

wherein said retention member further comprises a retention member first notch corresponding in location to said pad member first notch and a retention member second notch corresponding in location to said pad member second notch;

wherein said retention member first notch is larger than said pad member first notch;

wherein said main body member further comprises a main body first notch corresponding in location to said pad member first notch and a main body second notch corresponding in location to said pad member second notch;

wherein said lower adhesive layer covers the entire said underside of said main body member, and wherein said upper adhesive layer covers only a portion of said upper side of said main body member, such that the portion of said upper side of said main body member adjacent said main body ends are not covered by adhesive; and wherein the pad member is affixed to said main body member by a portion of said upper adhesive layer.

\* \* \* \* \*